United States Patent
Zahn et al.

(10) Patent No.: US 11,837,332 B2
(45) Date of Patent: Dec. 5, 2023

(54) SYSTEM AND METHOD FOR SAMPLE CHARACTERIZATION

(71) Applicant: Climax Foods Inc., Berkeley, CA (US)

(72) Inventors: Oliver Zahn, Berkeley, CA (US); Karthik Sekar, Berkeley, CA (US)

(73) Assignee: Climax Foods Inc., Berkeley, CA (US)

( * ) Notice: Subject to any disclaimer, the term of this patent is extended or adjusted under 35 U.S.C. 154(b) by 0 days.

(21) Appl. No.: 18/112,103

(22) Filed: Feb. 21, 2023

(65) Prior Publication Data

US 2023/0268034 A1    Aug. 24, 2023

Related U.S. Application Data

(60) Provisional application No. 63/311,896, filed on Feb. 18, 2022.

(51) Int. Cl.
*G16C 20/10* (2019.01)
*G16C 20/30* (2019.01)

(52) U.S. Cl.
CPC ............ *G16C 20/10* (2019.02); *G16C 20/30* (2019.02)

(58) Field of Classification Search
CPC ........... G16C 20/10; G16C 20/30; G16B 5/30
See application file for complete search history.

(56) References Cited

U.S. PATENT DOCUMENTS

| 11,185,095 | B2 * | 11/2021 | Molero Mendez | A23C 21/026 |
| 2018/0105836 | A1 * | 4/2018 | Sarma | C12N 1/32 |
| 2019/0218576 | A1 * | 7/2019 | Pachapur | C12P 3/00 |

FOREIGN PATENT DOCUMENTS

| CN | 110544507 A | * 12/2019 | ............. G16B 50/00 |

OTHER PUBLICATIONS

Watson, Elaine, "Climax Foods raises $7.5m: 'We want to replace animals as inefficient factories for converting plants into meat and dairy'", FoodNavigator-usa.com, Sep. 2, 2020.

* cited by examiner

*Primary Examiner* — Tung S Lau
(74) *Attorney, Agent, or Firm* — Jeffrey Schox; Diana Lin

(57) ABSTRACT

In variants, the method can include: determining a set of fermentation parameters; determining a set of features associated with the set of fermentation parameters; and determining a set of product attributes associated with the set of features. In examples, the method can optionally predict the attributes of a product manufactured using the set of fermentation parameters and/or predict the set of fermentation parameters that would create or replicate the attributes of a target product.

11 Claims, 11 Drawing Sheets

SYSTEM AND METHOD FOR SAMPLE CHARACTERIZATION

CROSS-REFERENCE TO RELATED APPLICATIONS

This application claims the benefit of U.S. Provisional Application No. 63/311,896 filed 18 Feb. 2022, which is incorporated in its entirety by this reference.

TECHNICAL FIELD

This invention relates generally to the food science field, and more specifically to a new and useful system and method for predicting product attributes in the food science field.

BACKGROUND

Conventionally, predicting the outputs of a fermentation process can be extremely difficult due to complex microbial interactions with other microbes (e.g., of the same or different type), with ingredients or byproducts, and/or with the process environment (e.g., temperature, pressure, O2 level, etc.).

Furthermore, because of the complex microbial pathways involved in creating a fermented product, it is incredibly difficult to determine which fermentation parameters (e.g., microbial cultures, ingredients, environmental conditions, etc.) would result in a fermented product with the desired characteristics.

Thus, there is a need in the food science field to create a new and useful system and/or method for predicting a fermentation output and/or determining the parameters for producing a target fermentation output.

DETAILED DESCRIPTION

The following description of the embodiments of the invention is not intended to limit the invention to these embodiments, but rather to enable any person skilled in the art to make and use this invention.

1. Overview

Figure 1:
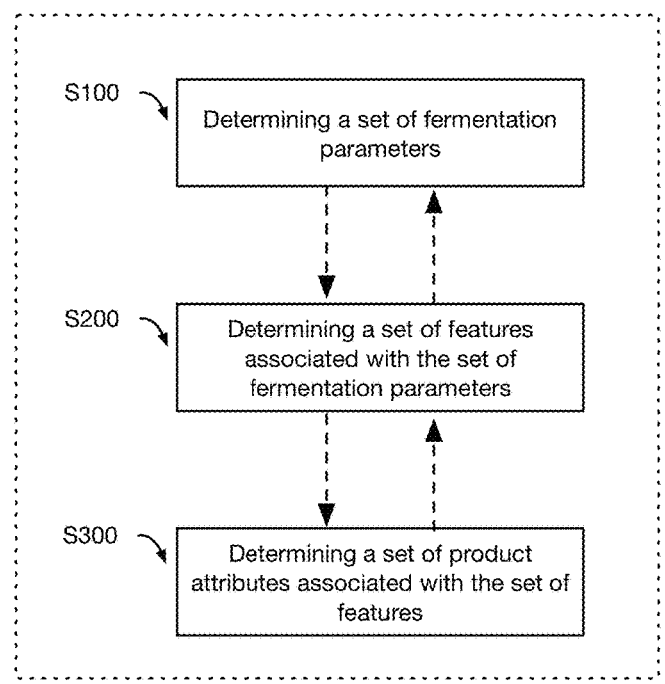
FIG. 1 is a schematic representation of a variant of the method.

Variants of the method can include: determining a set of fermentation parameters S100; determining a set of features associated with the set of fermentation parameters S200; and determining a set of product attributes associated with the set of features S300; example shown in FIG. 1. In a first variant, the method predicts the attributes of a product manufactured using the set of fermentation parameters. For example, this method can predict a product's compounds and flavors based on the microbial culture, the ingredients, and the sample's production environment. In a second variant, the method can predict the set of fermentation parameters that would create or replicate the attributes of a target product. For example, the method can predict the microbial cultures, ingredients, and process parameters that would manufacture a product having a target flavor, set of chemical compounds, mouthfeel, and/or other target functional property value.

2. Technical Advantages

Variants of the technology can confer several technical advantages over conventional methods.

First, variants of the technology can minimize the amount of experimental work required to determine product attribute values and/or determine which set of fermentation parameters to test by performing the experiments in silico. This can speed up experimentation and discovery, decrease the physical waste generated through these experiments, and decrease the cost of development. In examples, wet lab procedures can be replaced with a set of models (e.g., neural networks) that predict the result of the product manufacturing experiment.

Second, variants of the technology can reduce the modeling complexity previously required to determine a fermentation output by leveraging neural networks and/or other machine learning technologies. In examples, the neural networks can automatically learn the microbial interactions and metabolic pathways that produce the fermentation outputs given a set of fermentation parameters. Variants of the technology can also offer explainability (e.g., using interpretable deep learning, explainability methods, latent variables associated with semantics, etc.), which can offer insights into the models' predictions, and/or provide guidance on what fermentation parameters to adjust to achieve a target fermentation output.

However, further advantages can be provided by the system and method disclosed herein.

3. Method

As shown in FIG. 1, variants of the method can include: determining a set of fermentation parameters S100; determining a set of features associated with the set of fermentation parameters S200; and determining a set of product attributes associated with the set of features S300.

All or portions of the method can be performed once, repeated, iteratively performed, performed responsive to occurrence of an event (e.g., responsive to the product attributes differing from the target attributes by a threshold amount), periodically, and/or at any other suitable time. All or portions of the method can be performed in real time, contemporaneously, asynchronously, in parallel, serially, and/or with any other suitable relationship. All or portions of the method can be performed automatically, manually, semi-automatically, and/or otherwise performed.

The method can be used to predict the attributes of, or determine how to manufacture, a product. The product is preferably a food product, more preferably a fermented product, but can be any other suitable product. The food product is preferably a plant-based version (e.g., analog) of an animal product (e.g., target product), but can be an animal-based version of another animal product or a plant-based product, a cheaper version of a food product, and/or any other suitable food product. Examples of target food products include: dairy fats (e.g., ghee, other bovine milk fats, etc.), milk, curds, cheese (e.g., hard cheese, soft cheese, semi-hard cheese, semi-soft cheese), butter, yogurt, cream cheese, dried milk powder, cream, whipped cream, ice cream, coffee cream, other dairy products, egg products (e.g., scrambled eggs, egg whites, etc.), additive ingredients (e.g., functional ingredients, ingredients that confer a desired functionality or function in a particular manner, etc.), mammalian meat products (e.g., ground meat, steaks, chops, bones, deli meats, sausages, etc.), fish meat products (e.g., fish steaks, filets, etc.), any animal product, and/or any other suitable food product. In specific examples, the target food product includes mozzarella, burrata, feta, brie, ricotta, camembert, chevre, cottage cheese, cheddar, parmigiano, pecorino, gruyere, edam, gouda, jarlsberg, and/or any other cheese.

The plant-based food product can be vegan, vegetarian, include one or more animal-derived ingredients (e.g., microbial cultures, enzymes, proteins, etc.), and/or have any other suitable composition. The product can include only plant ingredients, mostly plant ingredients (e.g., more than 50%, 60%, 70%, 80%, 90%, 95%, or 99% plant ingredients, less than 10%, 5%, 1%, or 0.1% non-plant ingredients, etc.), and/or any other suitable proportion of plant ingredients (e.g., excluding the microbial cultures). Examples of plant ingredients can include: whole ingredients (e.g., ground plants, plant ingredients with minimal or no chemical processing, etc.), extracts (e.g., protein isolates, sugar extracts, flavor extracts, lipid extracts, milk extracts, cream extracts, etc.), and/or other ingredients. Examples of plants that can be used include: hemp, seeds (e.g., pumpkin seed, watermelon seed, etc.), legumes (e.g., pea, lentil, etc.), nuts (e.g., coconut, cashew, etc.), grains (e.g., oat, wheat, etc.), and/or other products. The product can optionally exclude and/or include less than a threshold amount of total and/or added: animal products (e.g., excludes animal proteins, such as caseins), gums (e.g., polysaccharide thickeners), allergenic ingredients (e.g., soy, peanut, wheat, etc.), and/or any other suitable ingredient. Added ingredients and/or compounds can include: materials that were not present in and/or are foreign to a plant substrate or other ingredients, materials added in as a separate ingredient, and/or otherwise other components. The threshold amount can be between 0.1%-50% or any range or value therebetween (e.g., 40%, 30%, 10%, 5%, 3%, 2%, 1%, 0.1%, etc.), but can alternatively be greater than 10% or less than 0.1%.

The product can be characterized by a set of product attributes. Examples of product attributes can include: sensory attributes, chemical attributes, physical attributes, and/or other attributes (e.g., functional properties).

Sensory attributes can include: flavor characteristics, taste characteristics (e.g., gustation intensity, pre-mastication taste, aftertaste, finish, etc.), texture characteristics (e.g., texture profile, firmness, toughness, puncture, stretch, compression response, mouthfeel, viscosity, graininess, relaxation, stickiness, chalkiness, flouriness, astringency, crumbliness, stickiness, stretchiness, tearability, mouth melt, etc.), appearance characteristics (e.g., color, sheen, etc.), odor characteristics (e.g., aroma, retronasal aroma, orthonasal aroma, olfactory bulb aroma, etc.), and/or characteristics for other sensory modalities. Sensory attributes are preferably perceived characteristics, but can additionally or alternatively be measured and/or inherent characteristics. The sensory characteristics can include: a quality (e.g., odor quality, such as "apple" or "buttery,"; taste quality, such as "salty" or "sweet"; etc.), an intensity, hedonic tone, and/or any other characteristic. The sensory attribute value can be: subjective (e.g., ranking), objective (e.g., a score, a relative or absolute amount, a relative or absolute intensity, etc.), semantic (e.g., "salty"), continuous, discrete, and/or otherwise configured. The sensory attributes (e.g., attribute values) for a product can be determined: using a sensory panel (e.g., manually), using a model trained to infer the sensory attribute based on chemical compound measurements, measured (e.g., using GC-MS, SIFT-MS, EEG, EKG, etc.; from breath expelled through the mouth or nose, from a vial headspace, from the product itself; etc.), estimated based on literature, and/or otherwise determined. In examples, the systems and/or methods described herein can use the systems and/or methods described in U.S. application Ser. No. 18/107,294 filed 8 Feb. 2023 titled "SYSTEM AND METHOD FOR SENSORY CHARACTERIZATION", which is incorporated herein in its entirety by this reference, and/or otherwise determined.

Chemical attributes can include: the chemical compounds present in the product (e.g., molecular composition), metabolites, the nutritional profile (e.g., micronutrient profile, macronutrient profile, etc.), chemical structure, the reactions and/or metabolic pathways capable of producing a given chemical compound (e.g., flavor compound), classes thereof (e.g., metabolite class, structure class, reaction class, etc.), ion binding capacity, chemical properties (e.g., pH, affinity, surface charge, isoelectric point, hydrophobicity/hydrophilicity, chain lengths, chemical composition, nitrogen levels, chirality, stereospecific position, etc.), and/or other chemical attributes. Chemical attributes can be: measured (e.g., using mass spectrometry), predicted, and/or otherwise determined.

Physical attributes can include: matrix characteristics (e.g., matrix type, matrix density, matrix porosity, etc.), texture (e.g., texture profile, firmness, toughness, puncture, stretch, compression response, mouthfeel, viscosity, graininess, relaxation, stickiness, chalkiness, flouriness, astringency, crumbliness, stickiness, stretchiness, tearability, mouth melt, etc.), solubility, melt profile, smoke profile, gelation point, precipitation, stability (e.g., room temperature stability), emulsion stability, physiochemical properties, denaturation point, denaturation behavior, aggregation point, aggregation behavior, particle size, structure (e.g., microstructure, macrostructure, fat crystalline structure, etc.), fat leakage, water holding and/or binding capacity, fat holding and/or binding capacity, fatty acid composition (e.g., percent saturated/unsaturated fats), moisture level, turbidity, and/or other physical attributes. Physical attributes can be: measured (e.g., using mass spectrometry), predicted, and/or otherwise determined.

In examples, the product attributes can be determined using the systems and/or methods described in U.S. application Ser. No. 18/098,898 filed 19 Jan. 2023, which is incorporated herein in its entirety by this reference. However, the product attributes can be otherwise determined.

Figure 2:
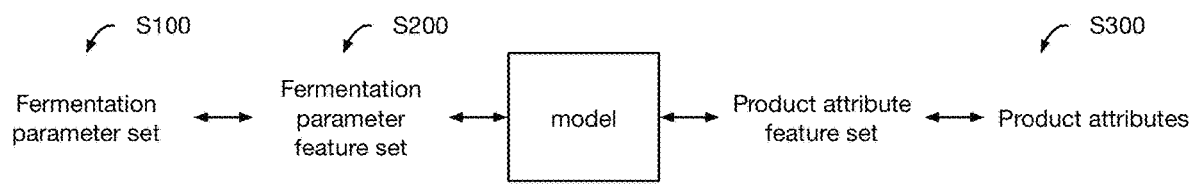
FIG. 2 is a schematic representation of an example of the method.
Figure 15:
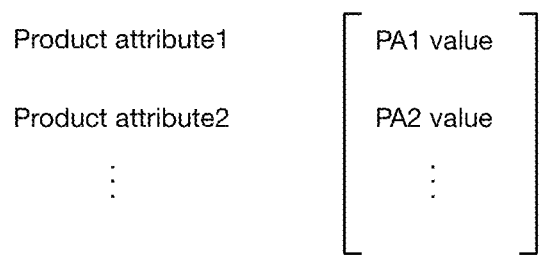
FIG. 15 is an illustrative example of a product attribute feature vector.

In variants, the product attributes can be parametrized (e.g., into a feature set) and/or associated with a set of features (e.g., example shown in FIG. 2). The set of features can be represented as a feature vector, as a feature space, and/or otherwise represented. Different attribute classes can be represented in the same or different set of features. For example, sensory attributes can have a first feature vector, physical attributes can have a second feature vector, and chemical attributes can have a third feature vector; alternatively, the attributes can share a single feature vector. The features can be determined by: mapping attribute values to the vector index for the respective parameter; using feature extraction methods (e.g., signal extraction methods, principal component analysis, dimensionality reduction, autoencoders, partial least squares, dimensionality reduction techniques, etc.); by encoding a semantic value as a quantitative value; and/or otherwise encoding the product attribute values into features. The values in the feature vector can represent: inclusion or exclusion, amount (e.g., concentration, relative amount, absolute amount, measurable value, etc.), score, valence, and/or other information In a first variant, the features can be the attributes (e.g., the attribute classes), and the feature values can be the attribute presence or absence in the product, and/or be the value for the respective value (e.g., example shown in FIG. 15). For example, each vector index in a feature vector can represent a different attribute class (e.g., a different flavor class, such as "buttery", "floral", etc.), and the value located at the vector index position can represent whether the attribute class is present in the product and/or the score (e.g., relative amount, absolute amount, intensity, etc.) of the associated attribute class. In variants, this feature vector can encode both the presence/absence of a sensory attribute, and also encode the amount of the sensory attribute. In an illustrative example, a vector of [0.9, 0.1, 0] can represent a product with a butteriness score of 0.9, a floral score of 0.1, and coffee score of 0 (e.g., the product does not have coffee notes).

In a second variant, the set of features can be described using a set of vectors, wherein the first vector can indicate whether a product attribute is present or absent within the product, and a second vector can include values indicative of the scores for the product attributes. In a first example, the second vector includes values for all attributes represented in the first vector. In a second example, the second vector only includes values for attributes present in the first vector (e.g., wherein the vector indices in the second vector can be dynamically remapped based on the values of the first vector). However, the vectors can be otherwise configured.

However, the product attributes can be otherwise parametrized and/or represented.

Figure 9:
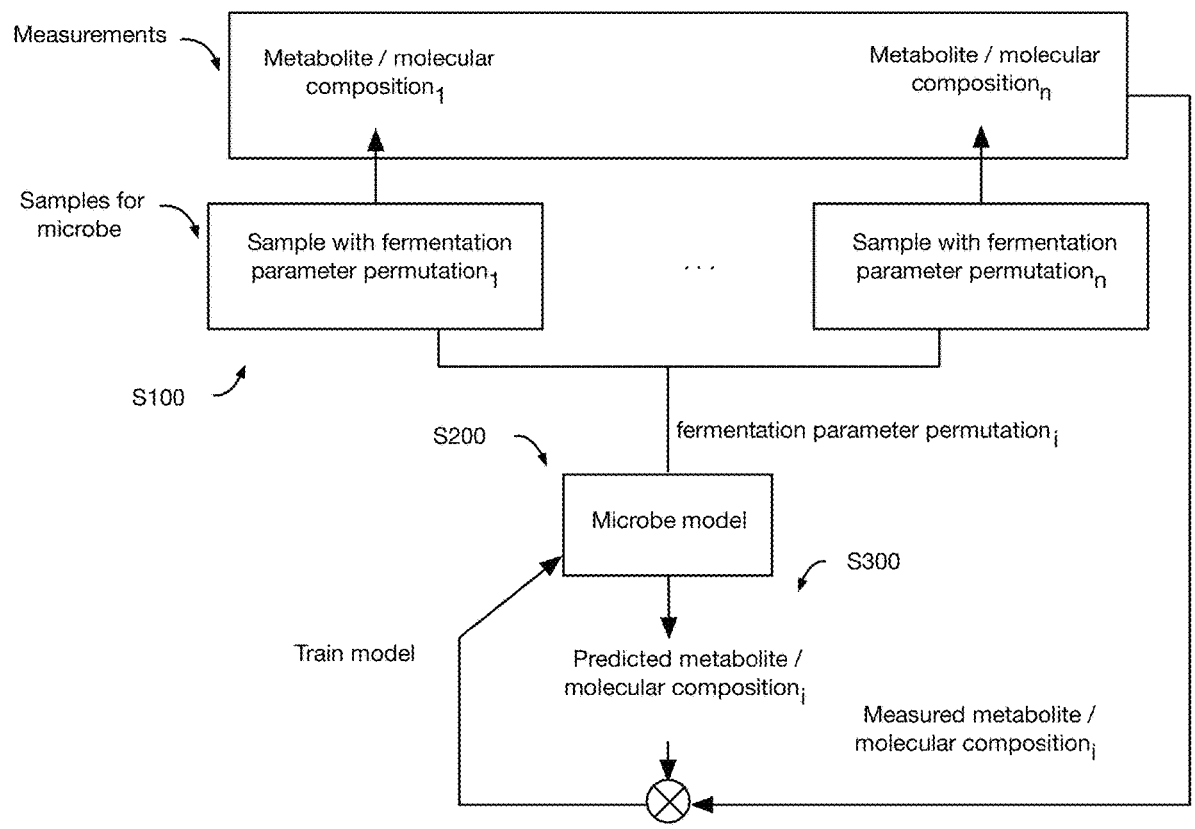
FIG. 9 is a schematic representation of a specific example of determining the product attributes.
Figure 19:
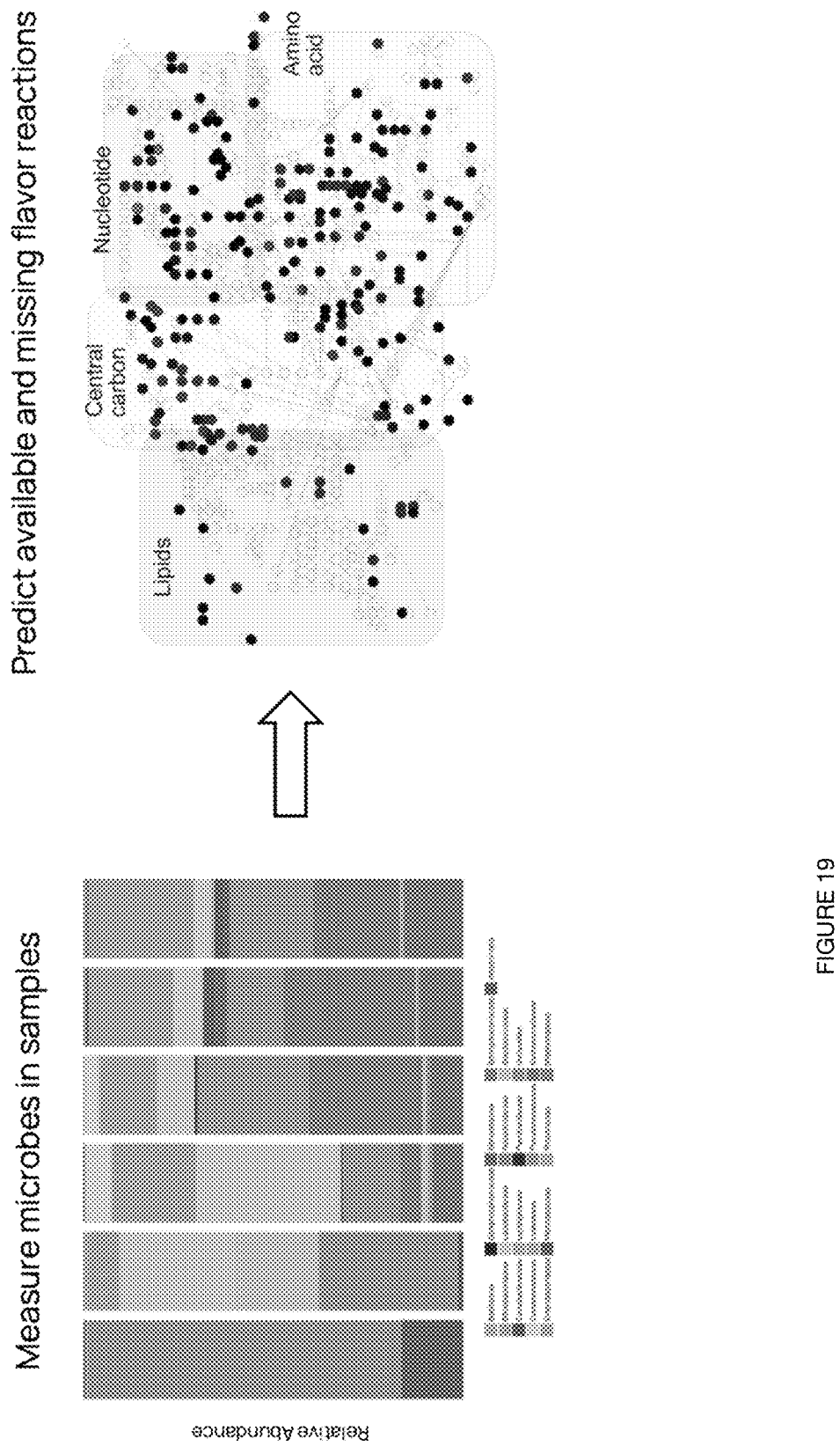
FIG. 19 is an illustrative example of identifying missing flavor compounds and adjusting process parameters to generate the missing flavor compounds.

Variants of the method can be performed using one or more models. For example, variants of the method can use: a product attribute model (e.g., configured to predict the product attributes given a set of fermentation parameters and/or features thereof); a fermentation parameter model (e.g., configured to predict the fermentation parameters that can be used to produce a product with a target set of product attributes; the same or different model as the product attribute model); microbial models (e.g., microbial networks; a set of metabolic models configured to determine the chemical and/or physical attributes given a set of starting ingredients and environmental conditions; a neural network trained to predict the metabolic composition and/or expressed metabolic pathways given a set of starting ingredients and conditions, examples shown in FIG. 9 and FIG. 19; etc.); and/or other models. The models can be automatically generated, manually generated, or otherwise generated. For example, a microbial network model can be automatically generated using known sequence information (e.g., from Kbase), retrieved from a third party service, or otherwise determined. In a second example, the edges of a microbial network model can be predicted using the genetics of the microbes within the microbial culture. In an illustrative example, this can include: determining the genome of the microbes in the culture, determining whether the genes associated with a predetermined set of enzymes are present in the determined genome, and predicting the edge or weight values of the microbial network based on the gene presence or absence. In a related example, the enzyme-related RNA expressions by the microbes can be determined, and the edge or weight values of the microbial network (e.g., associated with the respective enzyme) can be determined based on the RNA expression.

In examples, the models can be combined into a cascade or ensemble, used individually, or otherwise used. For example, a first model can predict inclusion or exclusion of specific fermentation parameters, while a second model can predict the values for the included fermentation parameters. In another example, a first model can predict the metabolites (e.g., metabolite composition) for a given set of fermentation parameters, while a second model can predict the product attribute values (e.g., flavor, odor, etc.). However, the set of models can be otherwise structured. In an illustrative example, metabolite compositions can be determined based on a set of fermentation parameters using aa microbial model that was trained on experimentally-derived metabolite compositions for products manufactured using each of a set of training fermentation parameters, and product attributes can be determined based on the metabolite compositions using a product attribute model trained on observed sensory attributes associated with each of a set of training metabolite compositions.

The models can be: generic, specific to a microbial culture, specific to a set of ingredients, specific to a set of process parameters, specific to a set of target attribute values, generic across microbial cultures, ingredients, process parameters, attribute values, product attributes, and/or otherwise generic or specific. In an illustrative example, the models can predict the flavors, flavor compound composition (e.g., which compounds and amount of each), and/or the reactions that can be produced by a given microbial culture given a set of ingredients and process parameters.

Figure 7:
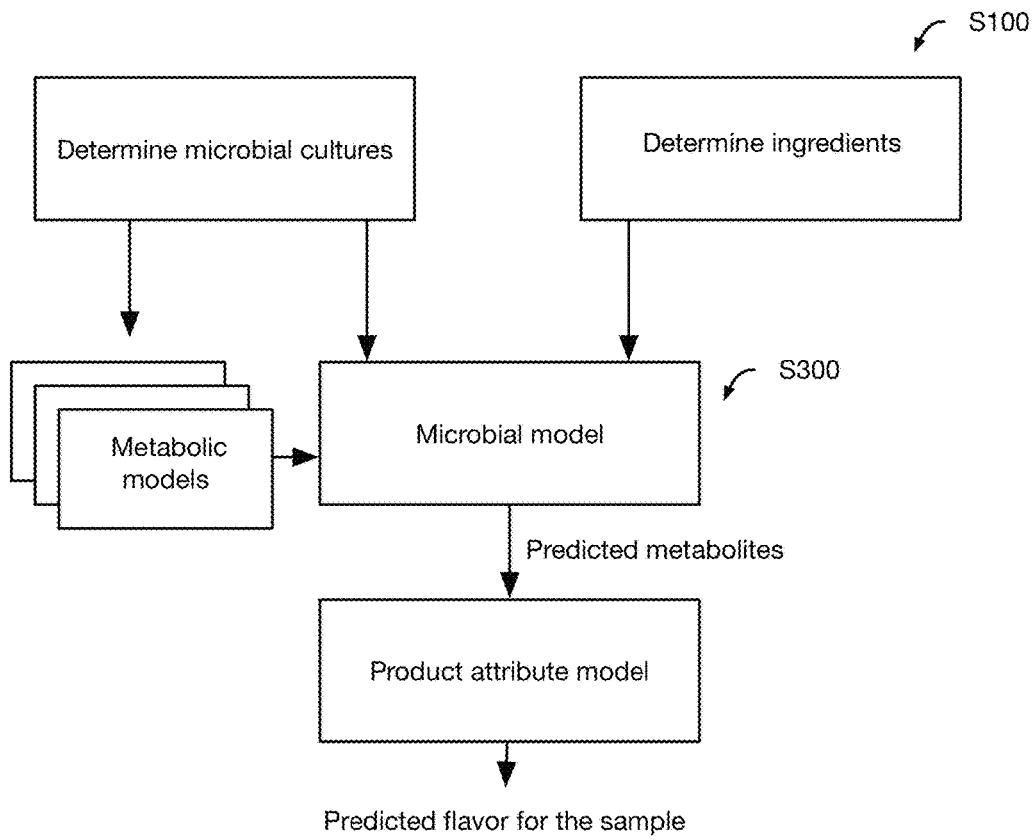
FIG. 7 is a schematic representation of a specific example of determining the product attributes.

One or more of the models can include or use classical machine learning models (e.g., regularization, linear regression, logistic regression, decision tree, SVM, nearest neighbor, PCA, SVC, LDA, LSA, t-SNE, naive bayes, k-means clustering, clustering, association rules, dimensionality reduction, kernel methods, genetic programs, support vectors, etc.), neural networks (e.g., CNN, CAN, LSTM, RNN, autoencoders, deep learning models, etc.), ensemble methods, rules, heuristics, deterministics, classification, equations (e.g., weighted equations, etc.), selection (e.g., from a library), optimization methods (e.g., Bayesian optimization. multi-objective Bayesian optimization, Bayesian optimal experimental design, etc.), Markov methods (e.g., hidden Markov models), statistical methods, probability methods, comparison methods (e.g., matching, distance metrics, thresholds, etc.), mass balances (e.g., metabolic models), a combination thereof, and/or any other suitable method or model. For example, the product attribute model can predict a set of product attributes based on a set of fermentation parameters and/or features thereof, wherein the metabolic model (e.g., a set of interrelated reaction equations) can be used to impose constraints on the model (e.g., used as a side channel input to the product attribute model; example shown in FIG. 7; etc.) and/or used to filter the model outputs (e.g., eliminate low-probability outputs).

In variants, the method can optionally use the outputs from intermediate layers of a model that was trained end-to-end to predict an output. For example, the method can include training a model (e.g., classifier) end to end to predict the product attribute set from a fermentation parameter set, then use an intermediate layer of the model (e.g., the fermentation parameter encoding, the product attribute encoding, etc.) to determine the similarity of a first product with a target product (e.g., with target product attribute values).

The models can be trained, learned, fit, predetermined, and/or can be otherwise determined. The models can be learned using: self-supervised learning, semi-supervised learning, supervised learning, unsupervised learning, reinforcement learning, transfer learning, Bayesian optimization, positive-unlabeled learning, using backpropagation methods, and/or otherwise learned.

Figure 8:
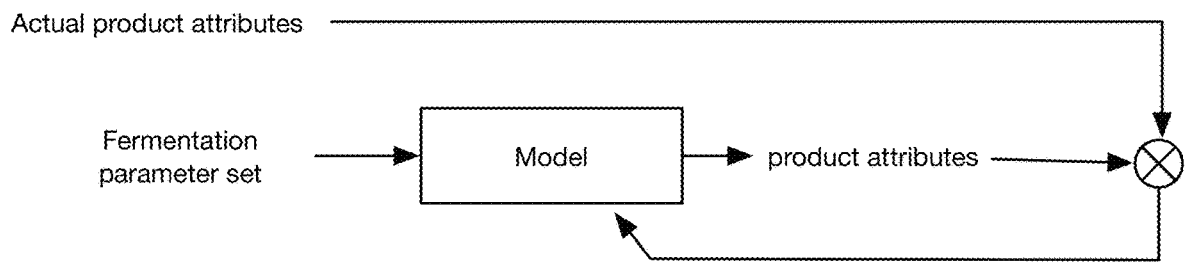
FIG. 8 is a schematic representation of an example of training a model.
Figure 10:
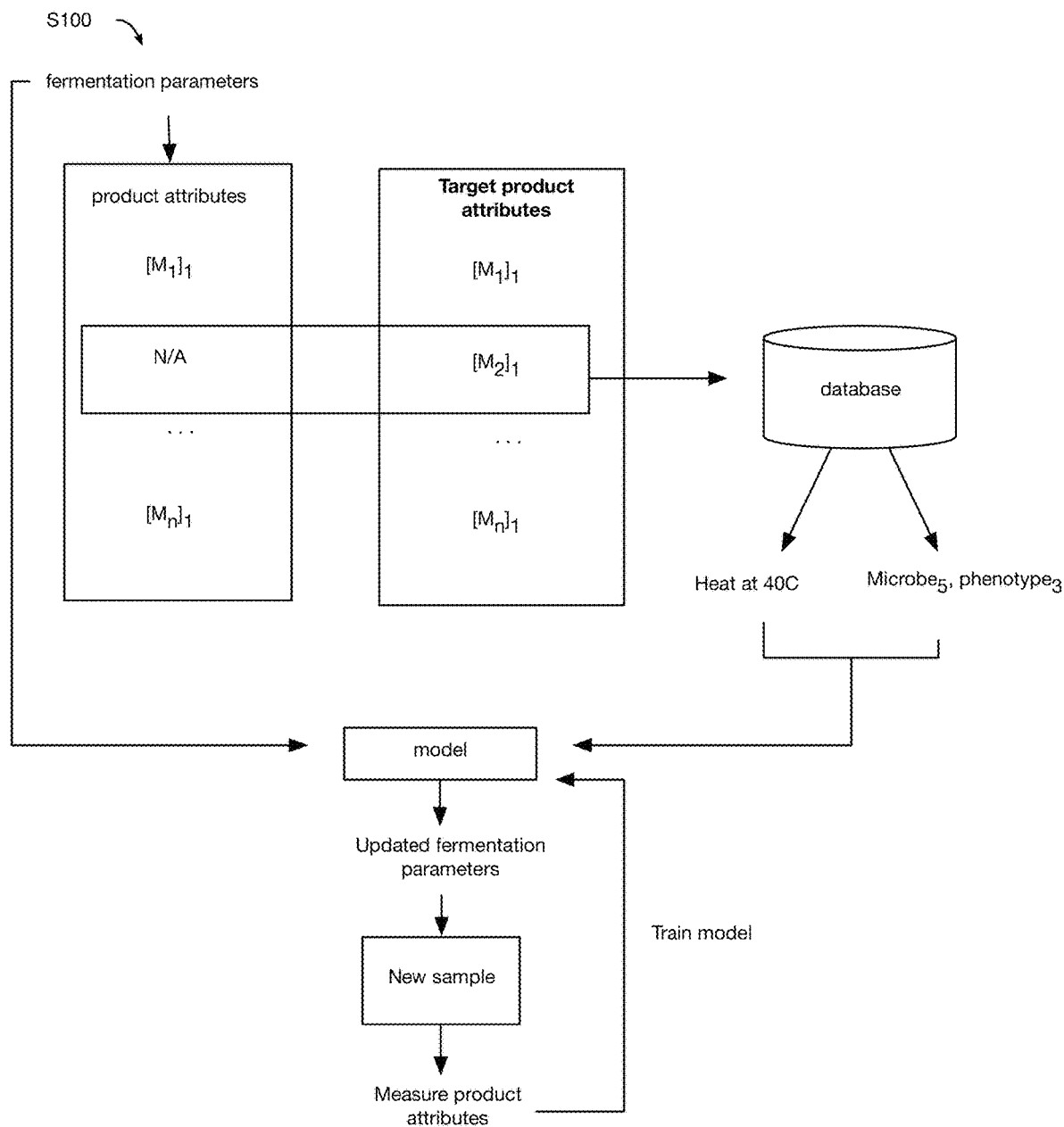
FIG. 10 is a first illustrative example of identifying missing compounds and adjusting the fermentation parameters to produce the compounds.

The models can be learned or trained on: labeled data (e.g., data labeled with the target label), unlabeled data, positive training sets (e.g., a set of data with true positive labels, negative training sets (e.g., a set of data with true negative labels), and/or any other suitable set of data. In a first example, training the attribute prediction model can include determining (e.g., measuring) a set of product attributes for a product manufactured using the fermentation parameter set, and training the attribute prediction model to predict the set of product attributes based on the fermentation parameter set (e.g., example shown in FIG. 8). In a second example, the model can be trained to predict the fermentation parameter set given the product attribute set (e.g., example shown in FIG. 16). In a third example, the model can be trained to determine a fermentation parameter set and/or change to a fermentation parameter set that brings the product closer to a set of target product attributes (e.g., based on a distance, similarity score, etc.). The training data is preferably experimental data (e.g., generated by manufacturing products using the set of fermentation parameters and measuring or otherwise obtaining the product attributes), but can alternatively be synthetic data and/or other data. The training data can be generated for each of a predetermined set of fermentation parameter permutations, be generated using an iterative exploration-exploitation method (e.g., wherein the product attributes of a prior product—and/or difference between the product's attributes and a set of target attributes—are used to determine which set of fermentation parameters should be tested next, examples shown in FIG. 10 and FIG. 11; wherein the fermentation parameter set is determined using Bayesian optimal experiment design; etc.), and/or for any other suitable set of fermentation parameters. For example, a model can be trained to predict product attribute values using a training data set including fermentation parameter values (and/or feature values) labeled with actual product attribute values (e.g., determined from measurements of the manufactured product); examples shown in FIG. 8. For example, models that are specific to a given fermentation parameter value (e.g., microbial culture, ingredients, process parameter, etc.) can be trained on experimental data for products made using fermentation parameter sets with the parameter value held constant while the other fermentation parameters are permuted across different experiments; alternatively, the specific models can be trained on experimental data without the fermentation parameter value and/or with different values.

The models and/or outputs thereof can optionally be explained or interpreted. Examples of explanation and/or interpretation methods that can be used include: local interpretable model-agnostic explanations (LIME), Shapley Additive explanations (SHAP), Layer-Wise Relevance Propagation, contrastive explanations method (CEM), counterfactual explanation, Protodash, Permutation importance (PIMP), L2X, partial dependence plots (PDPs), individual conditional expectation (ICE) plots, accumulated local effect (ALE) plots, Local Interpretable Visual Explanations (LIVE), generalized additive models with pairwise interactions (GA2Ms), Boolean Rule Column Generation, Generalized Linear Rule Models, Teaching Explanations for Decisions (TED), and/or any other suitable method and/or approach.

However, any other suitable model can be used.

Figure 3:
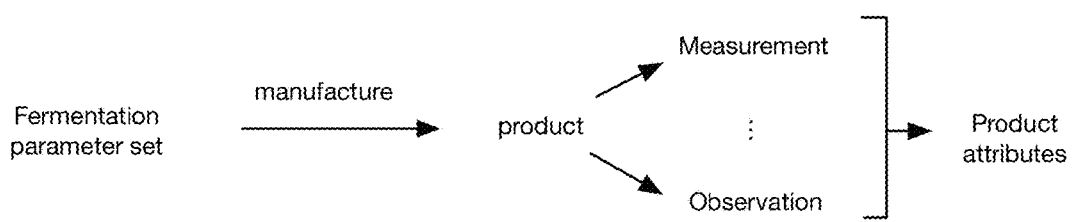
FIG. 3 is a schematic representation of an example of experimentally determining the product attribute set for a fermentation parameter set.

Variants of the methods described herein can be used with a set of fermentation parameters, which can specify the recipe for product manufacture (e.g., be used to manufacture the product, example shown in FIG. 3). The set of fermentation parameters can include: a set of ingredients, a set of microbial cultures, a set of process parameters, and/or any other suitable set of parameters. The set of fermentation parameters can specify: the fermentation parameter type (e.g., ingredient type, microbial culture type, process parameter type, etc.), a value for the fermentation parameter (e.g., ingredient amount, microbial culture amount, compound concentration, process parameter operation instruction, such as setting or timing, etc.), and/or any other suitable information.

Figure 14:
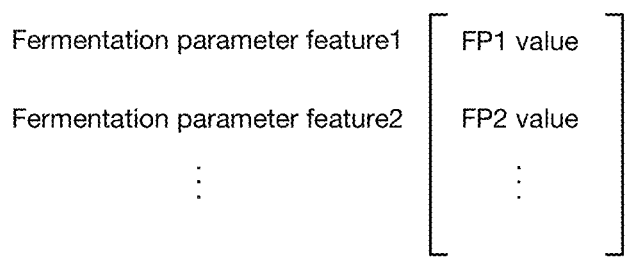
FIG. 14 is an illustrative example of a fermentation parameter feature vector.

In variants, the fermentation parameters can be parametrized (e.g., into a feature set) and/or associated with a set of features (e.g., example shown in FIG. 2). The set of features can be represented as a feature vector, as a feature space, and/or otherwise represented. Different fermentation parameters can be represented in the same or different set of features. For example, all fermentation parameter values for a given fermentation parameter set can be represented in a single vector. Alternatively, different fermentation parameter values for different fermentation parameter classes (e.g., compounds, ingredients, process parameters, etc.) can be represented in different vectors. The features can be determined by: mapping attribute values to the vector index for the respective parameter; using feature extraction methods (e.g., signal extraction methods, principal component analysis, dimensionality reduction, autoencoders, partial least squares, dimensionality reduction techniques, etc.); by encoding a semantic value as a quantitative value; and/or otherwise encoding the product attribute values into features. Fermentation parameter inclusion, valence, (e.g., quantity, proportion, amount, speed, other operational parameter, etc.), and/or other information can be represented: collectively as a single vector (e.g., the vector index represents a fermentation parameter or feature thereof, while the vector index value represents the fermentation parameter value or feature value; example shown in FIG. 14); multiple vectors (e.g., a first vector represents fermentation parameter or fermentation parameter feature inclusion, while a second vector represents the fermentation parameter or fermentation parameter feature values); and/or otherwise represented.

The ingredients can function as the inputs for the metabolic and/or other chemical reactions induced by the process parameters. The ingredient information can include: which ingredients, how much of each ingredient (e.g., absolute measure, relative measure, etc.), and/or other ingredient information. Examples of ingredients that can be used include: plant matter, proteins (e.g., protein isolates), lipids (e.g., fats, oils, etc.), an aqueous components (e.g., water, a sucrose solution, etc.), preservatives, acids and/or bases, macronutrients (e.g., protein, fat, starch, sugar, etc.), nutrients, micronutrients, carbohydrates (e.g., sugars, starches, fibers, polysaccharides, such as maltodextrin, gums, etc.), vitamins, enzymes (e.g., transglutaminase, chymosin, tyrosinase, bromelain, papain, ficain, other cysteine endopeptidases, rennet enzymes and/or rennet-type enzymes, etc.), emulsifiers (e.g., lecithin), particulates, hydrocolloids (e.g., thickening agents, gelling agents, emulsifying agents, stabilizers, etc,; such as starch, gelatin, pectin, and gums, such as agar, alginic acid, sodium alginate, guar gum, locust bean gum, beta-glucan, xanthan gum, etc.), salts (e.g., NaOH, NaCl, CaCl2, KCl, NaI, MgCl2, etc.), minerals (e.g., calcium), chemical crosslinkers (e.g., transglutaminase) and/or non-crosslinkers (e.g., L-cysteine), coloring, flavoring compounds, vinegar (e.g., white vinegar), mold powders, microbial cultures, carbon sources (e.g., to supplement fermentation), calcium citrate, any combination thereof, and/or any other ingredient. The ingredients can optionally exclude and/or include less than a threshold amount (e.g., 10%, 5%, 3%, 3%, 1%, 0.5%, 0.1%, etc.) of added: animal products, animal-derived ingredients, gums (e.g., polysaccharide thickeners), hydrocolloids, allergens, phospholipids, and/or any other suitable ingredient. The ingredients are preferably food-safe, but can alternatively be not food-safe. The ingredients can be whole ingredients (e.g., include processed plant material), ingredients derived from plant-based sources, ingredients derived from plant genes, synthetic ingredients, and/or be any other ingredient.

In variants, the ingredients can be parametrized (e.g., into a feature set) and/or associated with a set of features, wherein the set of ingredient features can be represented as described above, or be otherwise represented. In examples, the ingredient features can be: the ingredient identifier (e.g., ingredient itself), the ingredient's macronutrient class (e.g., fat, starch, sugar, etc.), the ingredient's micronutrient composition, the ingredient's chemical composition, the ingredient's functional properties (e.g., material properties, etc.), and/or other features. The values can represent the respective microbial culture feature's: amount (e.g., absolute amount, relative amount, etc.), presence or absence, and/or other value thereof.

The microbial cultures function to ferment the ingredients. The microbial cultures are preferably food-safe and/or regulatory-approved microbial cultures, but can alternatively be other cultures. The microbial culture information can include: which microbial culture, how much of each microbial culture (e.g., absolute measure, relative measure, etc.), and/or other microbial culture information. The microbial cultures can include a single microbe strain (e.g., genus, species, etc.), multiple microbe strains (e.g., in one or more proportions), and/or have any other suitable composition. Examples of microbial cultures that can be used include: cheese cultures (e.g., cheese starter cultures), yogurt cultures, wine cultures, beer cultures, and/or any other microbial culture. Examples of cheese cultures that can be used can include cultures for cheeses such as blue, camembert, cheddar, alpine, parmesan, swiss, and/or any other microbial culture and/or combination thereof. Examples of microbes that can be used include: *Arthrobacter arilaitensis, Arthrobacter bergerei, Arthrobacter globiformis, Arthrobacter nicotianae, Arthrobacter variabilis, Bifidobacterium adolescentis, Bifidobacterium animalis, Bifidobacterium bifidum, Bifidobacterium breve, Bifidobacterium infantis, Bifidobacterium lactis, Bifidobacterium longum, Bifidobacterium pseudolongum, Bifidobacterium thermophilum, Brachybacterium alimentarium, Brachybacterium tyrofermentans, Brevibacterium aurantiacum, Brevibacterium casei, Brevibacterium linens, Candida colliculosa, Candida kefyr, Candida jefer, Candida krusei, Candida mycoderma, Candida utilis, Candida vini, Candida zeylanoides, Carnobacterium divergens, Carnobactrium maltaromaticum, Corynebacterium ammoniagenes, Corynebacterium casei, Corynebacterium flavescens, Corynebacterium mooreparkense, Corynebacterium variabile, Cystofilobasidium infirmominiatum, Debaryomyces hansenii, Debaryomyces kloeckeri, Enterococcus faecalis, Fusarium domesticum, Geotrichum candidum, Hafnia alvei, Halomonas, Issatchenkia orientalis, Kazachstania exigua, Kazachstania unispora, Kluyveromyces lactis, Kluyveromyces marxianus, Kocuria rhizophila, Kocuria varians, Lactobacillus acidipiscis, Lactobacillus acidophilus, Lactobacillus brevis, Lactobacillus bulgaricus, Lactobacillus casei, Lactobacillus coryniformis, Lactobacillus curvatus, Lactobacillus delbrueckii, Lactobacilus fermentum, Lactobacillus gasseri, Lactobacillus johnsonii, Lactobacillus kefiranofaciens, Lactobacillus kefiri, Lactobacillus nodensis, Lactobacillus parabrevis, Lactobacillus paracasei, Lactobacillus parakefiri, Lactobacillus paraplantarum, Lactobacillus pentosus, Lactobacillus perolents, Lactobacillus planarum, Lactobacillus rhamnosus, Lactobacillus salivarius, Lactobacillus tucceti, Lactococcus lactis, Lactococcus raffinolactis, Lecanicillium lecanii, Leuconostoc citreum, Leuconostoc citovorum, Leuconostoc dextranicum, Leuconostoc pseudomesenteroides, Leuconostoc kimchi, Leuconostoc mesenteroides, Macrococcus caseolyticus, Microbacterium foliorum, Microbacterium gubbeenense, Micrococcus luteus, Pediococcus, Penicillium album, Penicillium camemberti, Penicillium caseifulvum, Penicillium chrysogenum, Penicillium commune, Penicillium nalgiovense, Penicillium roqueforti, Pichia fermentans, Propionibacterium acidipropionici, Propionibacterium freudenreichii, Propionibacterium jensenii, Proteus vulgaris, Psychrobacter celer, Rhodosporidium infirmominiatum, Rhodotorula minuta, Saccharomyces cerevisiae, Staphylococcus carnosus, Staphylococcus equorum, Staphylococcus fieurettii, Staphylococcus saphrophyticus, Staphylococcus sciuri carnaticus, Staphylococcus succinus, Staphylococcus vitulinus, Staphylococcus xylosus, Streptococcus cremoris, Streptococcus lactis, Streptococcus lactis subspecies diacetylactis, Streptococcus thermophilus, Streptococcus gallolyticus, Streptococcus sally arius, Thrichosporon beigelii, Verticillium lecanii, Yarrowia lipolytica,*

*Zygotorulaspora florentina*, the genuses thereof, the families thereof, the phyla thereof, and/or any other suitable microbe and/or combination thereof.

In variants, the microbial cultures can be parametrized (e.g., into a feature set) and/or associated with a set of features, wherein the set of microbial culture features can be represented as described above for the product attribute features, or be otherwise represented. In examples, the microbial culture features can be: the ingredient identifier (e.g., ingredient itself), the ingredient's macronutrient class (e.g., fat, starch, sugar, etc.), the ingredient's micronutrient composition, the ingredient's chemical composition, the ingredient's functional properties (e.g., material properties, etc.), and/or other features. The values can represent the respective ingredient feature's: amount (e.g., absolute amount, relative amount, concentration, etc.), presence or absence, and/or other value thereof.

Examples of microbial culture features that can be used include: the microbial culture identifier (e.g., identifying a mixture of multiple microbe strains), the compounds that the microbial culture can produce (e.g., the enzymes that the microbes in the culture can produce, the byproducts that the microbes in the culture can produce, etc.), the metabolic pathways (and/or pathway classes) that the microbial culture can express, the product attributes that the microbial culture can produce (e.g., the flavors that can be produced, the textures that can be produced, etc.), microbe features, and/or any other suitable set of microbial culture features. Examples of microbe features can include: genomic features (e.g., wherein each feature is a loci, nucleotide, or gene in the microbe's genome; metagenomics; etc.), transcriptomic features (e.g., each feature is a potential RNA that can be expressed), phenotype features, proteins or enzymes (e.g., each feature is a potential enzyme or protein that can be expressed), byproducts (e.g., each feature is a potential byproduct or compound that can be generated), functions (e.g., each feature is a function, pathway, or pathway class that the microbe can perform), sample attributes (e.g., each feature is a flavor, odor, texture, etc.), and/or other microbial features.

In an illustrative example, the vector index of a microbial culture feature vector can represent the potential RNA that can be expressed (e.g., for the microbial culture, across all microbial cultures), and the value can indicate whether and/or the amount (e.g., relative or absolute amount) of the given RNA that can be expressed by the microbial culture or is expressed by the microbial culture (e.g., given the process parameters). In a second illustrative example, the vector index of a microbial culture feature vector can represent the potential flavors supported by the method (e.g., all possible flavors that are being evaluated), and the value can indicate whether and/or how much of the flavor can be produced by the microbial culture, and/or how much of the flavor is produced by the microbial culture (e.g., given the process parameters). In a third illustrative example, the vector index of a microbial culture feature vector can represent the possible microbial cultures that can be used in the fermentation parameter set, and the value can indicate whether and/or how much of the microbial culture is used.

The process parameters function to define the manufacturing instructions for the product. The process parameters can include: which manufacturing process should be used, manufacturing parameters, temporal parameters (e.g., when a process, ingredient, or microbial culture should be applied, duration of input application, etc.); environmental conditions (e.g., temperature, pressure, pH, ionic strength, etc.), and/or any other suitable process parameter. Manufacturing parameters can include: ingredients, treatments, and/or any other sample manufacturing input, wherein the fermentation parameters can include parameters for each specification. Examples of treatments can include: adjusting temperature, adjusting salt level, adjusting pH level, diluting, pressurizing, depressurizing, humidifying, dehumidifying, agitating, resting, adding ingredients, removing components (e.g., filtering, draining, centrifugation, etc.), adjusting oxygen level, brining, comminuting, fermenting, mixing (e.g., homogenizing), gelling (e.g., curdling), and/or other treatments. Examples of treatment parameters can include: treatment type, treatment duration, treatment rate (e.g., flow rate, agitation rate, cooling rate, rotor stator rpm, etc.), treatment temperature, time (e.g., when a treatment is applied, when the sample is characterized, etc.), and/or any other parameters.

In variants, the process parameters can be parametrized (e.g., into a feature set) and/or associated with a set of features, wherein the set of process parameter features can be represented as described above for the product attribute features, or be otherwise represented. In examples, the process parameters features can be: the process parameter, an induced effect (e.g., agitation at a predetermined rate), the control instruction for the machine implementing the process parameter, and/or other features. The values can represent the respective process parameter feature's: amount (e.g., absolute amount, relative amount, etc.), presence or absence, and/or other value thereof.

In examples, the fermentation parameter set can be determined using the systems and/or methods described in U.S. application Ser. No. 18/098,898 filed 19 Jan. 2023, which is incorporated herein in its entirety by this reference.

However, the fermentation parameter set can be otherwise determined.

Determining a set of fermentation parameters S100 functions to determine the recipe that can be used to produce a product.

In a first variant, the fermentation parameter set is predetermined or known. For example, the fermentation parameter set (e.g., the values thereof) can be: manually specified, randomly determined, determined by permuting the possible fermentation parameter values, and/or otherwise determined.

Figure 18:
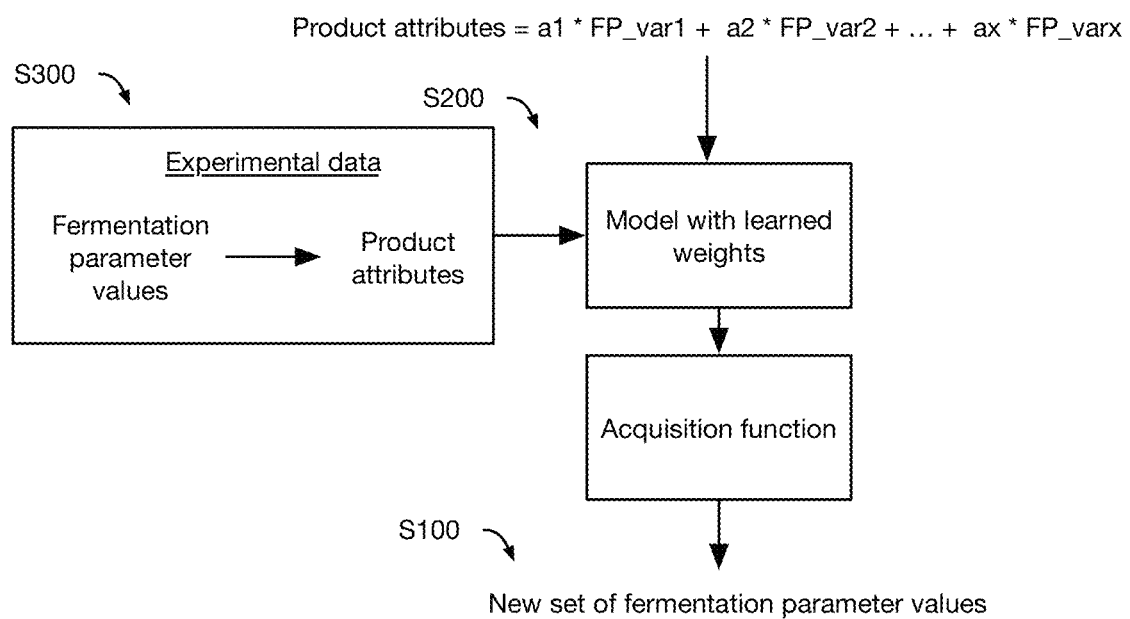
FIG. 18 is an illustrative example of determining a new fermentation parameter set using Bayesian optimization.

In a second variant, the fermentation parameter set is unknown, wherein S100 includes predicting the fermentation parameter set based on the product manufactured using a prior fermentation parameter set and/or a target attribute set (e.g., example shown in FIG. 18). For example, the fermentation parameter set can be determined using exploration-exploitation, using Bayesian optimization or Bayesian optimal experimental design (e.g., wherein the training data is fit to a surrogate function and the acquisition function predicts the fermentation parameter values based on the surrogate function that would minimize the difference between the product's attribute values and a target set of attribute values), by predicting a new fermentation parameter set based on the product attributes (and/or features thereof), and/or otherwise determined. The difference between the product attribute values and the target attribute values can be: a mathematical difference, a distance (e.g., cosine distance, vector distance, etc.), and/or any other suitable difference.

Figure 11:
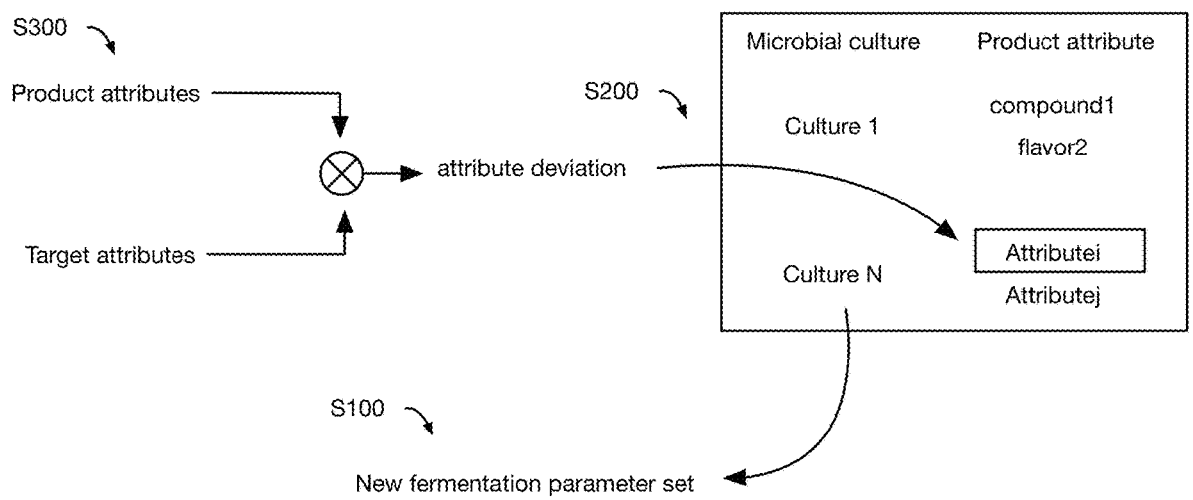
FIG. 11 is an illustrative example of identifying deviant product attributes and adjusting the fermentation parameters based on the product attribute deviation.

In first embodiment, a difference between the product attributes and target attributes can be determined (e.g., a deviant product attribute is determined), wherein a new fermentation parameter value associated with the difference can be selected (e.g., example shown in FIG. 11). In a first example, when a flavor compound is missing from the product attribute, a microbial culture that can produce the flavor compound can be included in the new set of fermentation parameters. In a second example, the manufacturing parameters can be adjusted (e.g., iteratively, based on a prediction, etc.) to produce the flavor compound.

Figure 12:
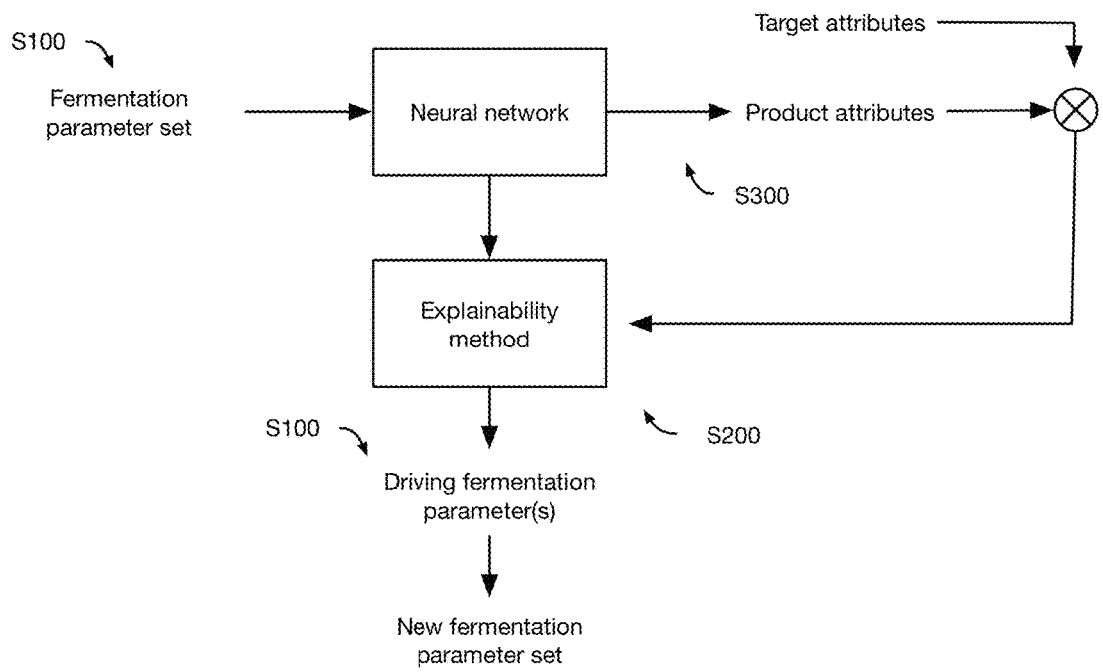
FIG. 12 is an illustrative example of determining a new fermentation parameter set using explainability methods.

In a second embodiment, the new set of fermentation parameters can be determined by: identifying a deviant product attribute, determining which model parameters (e.g., neural network weights, coefficients, etc.) and/or the features associated with the product attribute deviation (e.g., using explainability methods, etc.), and adjusting the fermentation parameters and/or feature values (e.g., example shown in FIG. 12). For example, an explainability score associated with a missing flavor compound can be associated with a process parameter (e.g., the semantics associated with the model parameters and/or influential features), wherein the new set of fermentation parameters can include an adjusted value for the process parameter. In another example, a subset of metabolites contributing to the set of deviant product attributes can be determined (e.g., using explainability methods, interpretable deep learning, etc.), wherein the new set of fermentation parameters can be determined based on the subset of metabolites. For example, ingredients or microbial cultures that produce a missing metabolite can be added; ingredients or microbial cultures that produce an excessive metabolite can be removed; fermentation parameters associated with a set of metabolic features, that, in turn, are associated with the set of metabolites can be adjusted (e.g., a desired change in the metabolic feature values can be determined and converted into the fermentation parameter values, such as by a decoder, by searching for fermentation parameter values that substantially match the adjusted metabolic feature values, etc.); and/or the new set of fermentation parameters can be otherwise determined.

In a third embodiment, the new set of fermentation parameters can be determined by predicting the fermentation parameter values using Bayesian optimization (e.g., wherein the fermentation parameters and/or features can be the independent variables and the product attributes and/or features can be the dependent variables).

Figure 13:
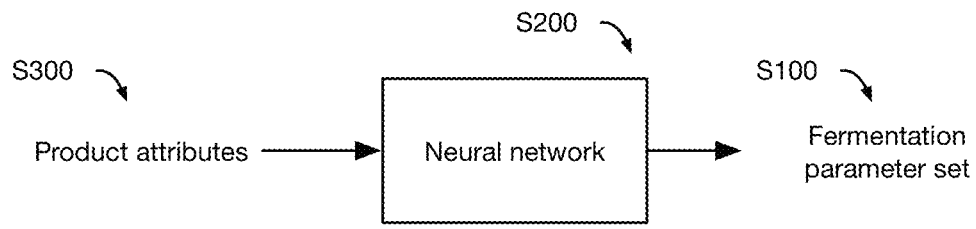
FIG. 13 is an illustrative example of determining a new fermentation parameter set using a neural network.

In a fourth embodiment, the new set of fermentation parameters can be determined by: generating a plurality of fermentation parameter sets (e.g., using the first variant of S100), predicting the product attributes for each fermentation parameter set (e.g., using S200 and S300), and selecting the fermentation parameter set that In a fifth embodiment, the new set of fermentation parameters can be determined by predicting the functional property values based on the target attribute values using a trained model (e.g., neural network); example shown in FIG. 13.

Figure 16:
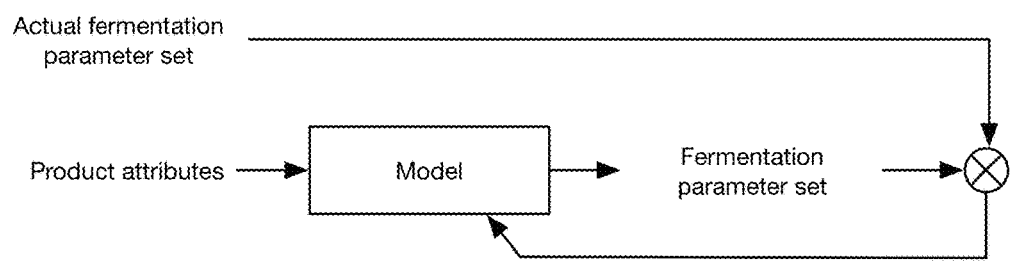
FIG. 16 is a schematic representation of training a model to predict the fermentation parameter set.

In a first example of the fifth embodiment, a neural network can be trained to predict the fermentation parameters and/or values thereof that will produce a target product with a set of target attributes (e.g., example shown in FIG. 16). In a specific example, the neural network can include multiple output heads (each representing a fermentation parameter) and/or predict a fermentation parameter vector, wherein each vector index represents a different fermentation parameter. The value predicted by the output head and/or the vector index value can be: the probability that the fermentation parameter will be relevant, the confidence interval for the prediction, the value for the fermentation parameter (e.g., temperature, agitation speed, incubation time, etc.), and/or represent any other suitable information.

In a second example, the neural network can be similar to the first example, but instead predict the change in the fermentation parameter values needed to achieve a change in the product attribute values.

Figure 17:
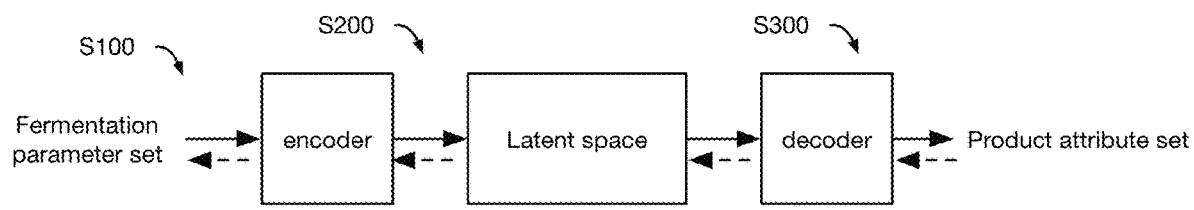
FIG. 17 is an illustrative example of determining a product attribute set based on a fermentation parameter set and/or determining a fermentation parameter set based on a product attribute set.

In a second example of the fifth embodiment, a neural network (e.g., autoencoder) can be trained to encode the fermentation parameters (e.g., the fermentation parameter features) and the product attributes (e.g., the product attribute features) into a common latent space, wherein the target attribute values (e.g., the target attribute feature vector) can be decoded into a set of fermentation parameter values (e.g., a set of fermentation parameter feature values, which can optionally be converted into fermentation parameter values) and/or vice versa; illustrative example shown in FIG. 17. In an illustrative example, an autoencoder can be trained to encode the microbial culture features and the product attributes (e.g., flavors, chemical composition, etc.) into a common latent space (e.g., into a common latent representation), wherein a deviation in a product attribute (e.g., the missing flavor, the odor that needs to be bolstered) can be decoded into a set of microbial culture feature values, wherein a microbial culture with the microbial culture feature values can be selected for inclusion in the new fermentation parameter set. in another illustrative example, the new set of fermentation parameters can include: determining a target latent representation for a set of target product attributes in the common latent space using the model (e.g., the decoder of a model trained to predict product attributes from fermentation parameters); and determining the target fermentation parameter set associated with the target latent representation. Determining the target fermentation parameter set associated with the target latent representation can include: decoding the latent representation into the target fermentation parameter set (e.g., using the encoder); identifying a known fermentation parameter set, associated with a latent representation similar to the target latent representation (e.g., based on a similarity score, etc.), from a fermentation parameter database; and/or otherwise determined.

In third example of the fifth embodiment, a neural network can be trained end-to-end to predict a product attribute set from a fermentation parameter set, wherein the output of an intermediate layer (e.g., the fermentation parameter embedding or feature vector, the product attribute embedding or feature vector, etc.; output by an encoder or decoder of an autoencoder, by a projection layer, and/or by any other suitable intermediate model layer, etc.) can be used to determine the new fermentation parameter set. In a first specific example, the product attribute embedding predicted for each of a plurality of fermentation parameter sets can be extracted and compared against the target product attribute set's features, wherein the fermentation parameter set with the closest product attribute embedding can be selected as the new fermentation parameter set. Additionally or alternatively, a set of deviant product attributes (e.g., missing attributes, excess attributes, etc.) can be determined based on the comparison, wherein fermentation parameters that rectify the product attribute deviation can be determined. For example, this can be performed by identifying the deviant fermentation parameters features contributing to the deviant product attributes, determining a set of resolution fermentation parameters features that would resolve the deviation, and searching through a database of known fermentation parameters associated with their respective fermentation parameter features to identify a set of fermentation parameters that have fermentation parameter features similar to the set of resolution fermentation parameters features.

In a sixth embodiment, the new set of fermentation parameters can be determined by: determining the product attribute set for each of a set of time steps (e.g., using a metabolic model, such as that described in the first variant of S300; using a trained neural network; etc.); selecting the product attribute set closest to the target attribute set; and determining the new set of fermentation parameters based on the fermentation parameters leading up to the selected product attribute set (e.g., the fermentation parameters associated with the selected product attribute set's timestep).

However, the set of fermentation parameters can be otherwise determined.

Determining a set of features associated with the set of fermentation parameters S200 can function to parametrize the fermentation parameters into a format that can be ingested by and/or output by a model. Additionally or alternatively, determining the feature set can function to determine the feature values, associated with a set of fermentation parameter values that can be used to manufacture a product with a target attribute set and/or desired attribute value change. Features can be determined by: mapping parameter values to the vector index for the respective parameter; using feature extraction methods (e.g., signal extraction methods, principal component analysis, dimensionality reduction, autoencoders, partial least squares, dimensionality reduction techniques, etc.); by encoding a semantic value as a quantitative value (e.g., encoding a microbial allele as −1, 0, 1 based on the allele frequency in the population, encoding an allele as 0 or 1 based on whether the allele is recessive or not, etc.); and/or otherwise encoding the fermentation parameter values into features.

In a first variant, the feature values are determined for a known fermentation parameter set. In this variant, the feature values can be: extracted (e.g., using a deterministic method, using a rule set, etc.), measured (e.g., using mass spectrometry, by measuring the starting microbial culture, etc.), looked up (e.g., from a database), and/or otherwise determined. For example, the feature values can include a parametrized version of the microbial culture. In a second example, the feature values can be measured (e.g., experimentally) for each of a set of fermentation parameters.

In a second variant, the feature values can be determined (e.g., using a model) for an unknown fermentation parameter set. In a first example, the feature values can be decoded from a common latent space shared with a set of product attribute features. In a second example, a model can be trained to predict the feature values based on product attribute features. However, the features can be otherwise determined.

In a third variant, the method can skip feature value determination.

However, the feature values can be otherwise determined.

Determining a set of product attributes associated with the set of features S300 can function to: predict the product attribute values for a product manufactured using a set of fermentation parameters (e.g., associated with the set of features). Additionally or alternatively, determining a set of product attributes can determine the target attribute values, determine the difference between a sample's attribute values and the target attribute values, and/or otherwise determine the product attributes.

In a first variant, the product attribute values are determined based on the feature values using a model. For example, product attribute values can be predicted using known fermentation parameter feature values.

Figure 4:
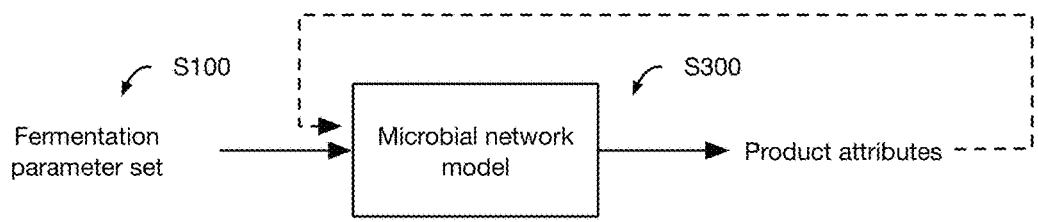
FIG. 4 is a schematic representation of a first embodiment of determining the product attribute.

In a first embodiment, a microbial network (e.g., set of reaction equations) can be used to predict the product attribute values at each of a set of timesteps, wherein the outputs of a prior timestep are used as the inputs to a subsequent timestep; examples shown in FIG. 4. Additionally or alternatively, the metabolites (e.g., metabolite composition, identities and amounts) and/or features thereof (e.g., extracted from an intermediary layer) can be used to determine (e.g., predict, look up, match, etc.) the product attribute set (e.g., the flavors, odors, etc.) for the product using a product attribute model (e.g., wherein the overall model includes a microbial submodel and a product attribute submodel).

Figure 5:
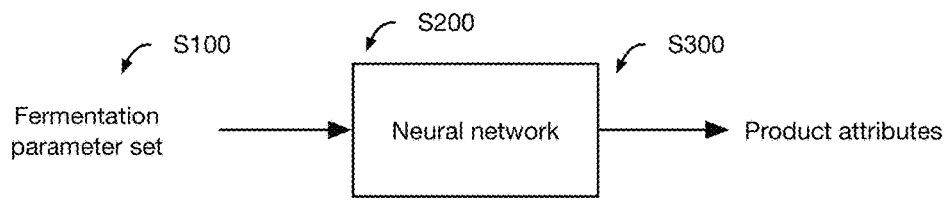
FIG. 5 is a schematic representation of a second embodiment of determining the product attributes.
Figure 6:
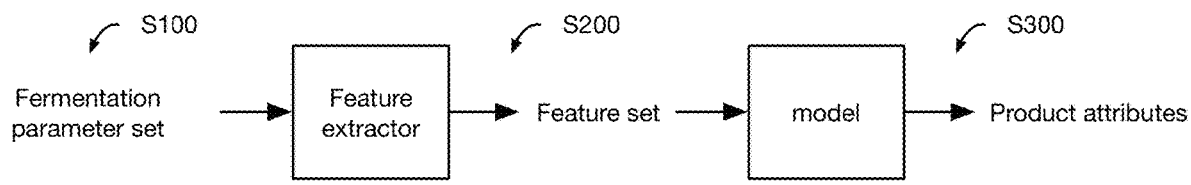
FIG. 6 is a schematic representation of an example of determining the product attributes.

In a second embodiment, the product attribute values are predicted by a neural network, given the fermentation parameter values (e.g., example shown in FIG. 5). For example, the product attribute values (and/or features thereof) can be predicted based on the fermentation parameter feature values determined based on the feature parameter values (e.g., example shown in FIG. 6). In this embodiment, the training data can include parametrized fermentation parameter sets labeled with the actual product attribute values (and/or feature values thereof) for the product manufactured using the respective fermentation parameter set, wherein the actual product's attribute values can be measured, observed by a user (e.g., a sensory panelist), or otherwise determined. In this embodiment, the neural network can be trained to predict the actual product attribute value (and/or feature value) based on the respective fermentation parameter feature values.

In a third embodiment, a hidden Markov model is used to determine the product attribute values, wherein the product attribute values can be treated as the observable process (e.g., Y), and how the metabolic culture creates the product attribute values can be treated as the Markov process (e.g., X). The HMM can be learned using the experimental product attribute values for one or more products manufactured using one or more fermentation parameter sets, and used to predict the product attribute values for theoretical fermentation parameter sets.

However, the product attribute values can be otherwise determined based on the fermentation parameter feature values.

In a second variant, the product attribute values can be directly determined, wherein the known product attribute values can be used to determine the fermentation parameter feature values. In this variant, the product attribute values can be: measured (e.g., using assays, tests, experiments, any of the methods disclosed above, etc.), observed (e.g., by a sensory panelist), rated, ranked, and/or otherwise determined. In a first example, the product attribute values can be target attribute values, such as that attribute values for the animal product to be replicated using plant-based ingredients. In a second example, the product attribute values are a difference between the attribute values of a manufactured product (e.g., sample) and the target attribute values. The difference can be a mathematical difference, comparison (e.g., cosine distance, etc.), and/or any other suitable difference. In variants, the target attribute values, attribute value difference, and/or other information can be converted into fermentation parameter feature values, then used to determine process attribute values (e.g., as described in the second variant of S100, the second variant of S200, and/or otherwise performed).

However, the method can be otherwise performed.

In a first illustrative example of the method, the method includes predicting the product attributes for a product manufactured using a set of fermentation parameters, including a set of ingredients, a set of microbial cultures, and a set of process parameters. In variants, this can include: determining a set of feature values for the set of fermentation parameters and predicting the product attributes based on the set of feature values. In an example, the product attributes are predicted using a trained model (e.g., neural network), which can output a vector wherein each vector index represents a different product attribute, and the vector index value represents the presence and/or amount (e.g., score, rating, ranking, concentration, etc.) of the product attribute within the product.

In a second illustrative example of the method, the method predicts a fermentation parameter set given a target attribute set. In a first variant, this can include: predicting the fermentation parameter values based on the target attribute set using a trained model. In an example, the target attribute set can be encoded into a common latent space, then decoded into the fermentation parameter space to determine the fermentation parameter values. In a second example, the model can predict the values for each of a set of fermentation parameters based on the values of the target attribute set (e.g., wherein the model includes an input or input vector index for each possible product attribute and an output or output vector index for each possible fermentation parameter). In a second variant, this can include: predicting the fermentation parameter feature values based on the target attribute set using a trained model, then determining the fermentation parameter values based on the fermentation parameter feature values (e.g., by using another model to determine the fermentation parameter values from the fermentation parameter feature values; by determining which fermentation parameter values have the fermentation parameter feature values; etc.).

In a third illustrative example of the method, the method predicts a fermentation parameter set given a desired product attribute adjustment. The desired product attribute adjustment can be determined based on a difference between the measured product attribute values for a manufactured product and a set of target attribute values, or otherwise determined. In examples, this can include: predicting the fermentation parameter adjustments based on the product attribute difference (e.g., the difference valence, amount, etc.) using a trained model.

However, the product attributes can be otherwise determined, and/or the fermentation parameter sets capable of manufacturing a product with a set of target attributes can be otherwise determined.

All references cited herein are incorporated by reference in their entirety, except to the extent that the incorporated material is inconsistent with the express disclosure herein, in which case the language in this disclosure controls.

Different processes and/or elements discussed above can be performed and controlled by the same or different entities. In the latter variants, different subsystems can communicate via: APIs (e.g., using API requests and responses, API keys, etc.), requests, and/or other communication channels. Communications between systems can be encrypted (e.g., using symmetric or asymmetric keys), signed, and/or otherwise authenticated or authorized.

Figure 20:
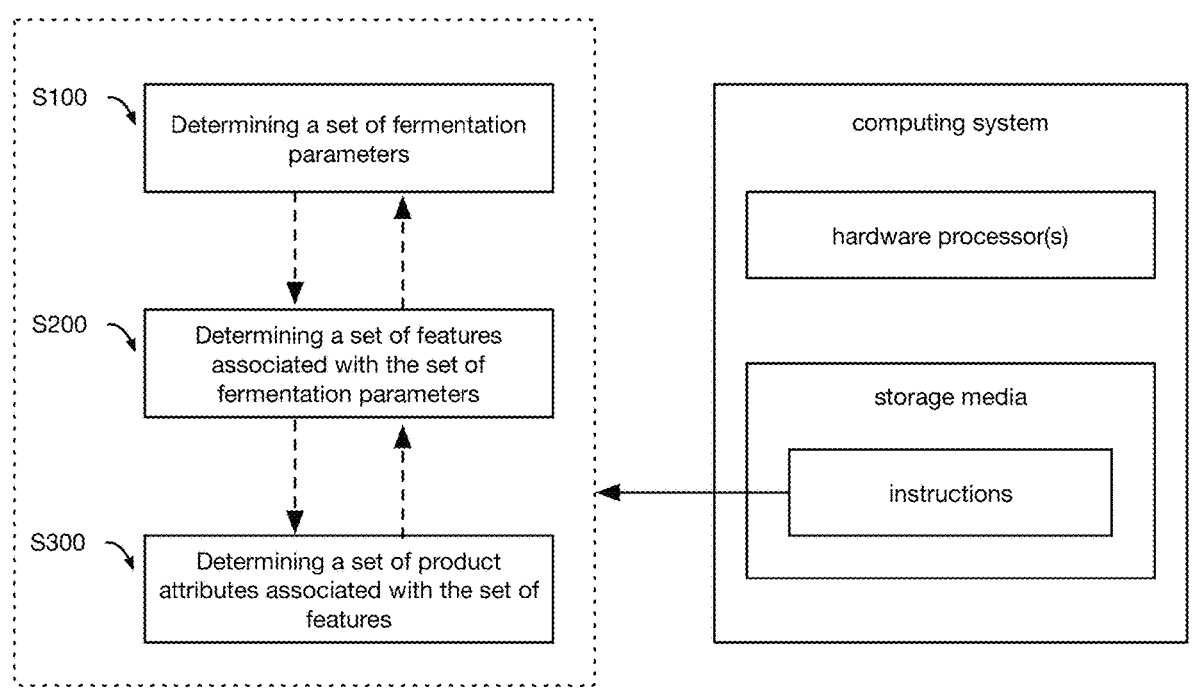
FIG. 20 is a schematic representation of a variant of the system.

Alternative embodiments implement the above methods and/or processing modules in non-transitory computer-readable media, storing computer-readable instructions that, when executed by a processing system, cause the processing system to perform the method(s) discussed herein. An example is shown in FIG. 20. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various elements (and/or variants thereof) discussed above, and/or omit one or more of the discussed elements, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the embodiments of the invention without departing from the scope of this invention defined in the following claims.

We claim:

1. A computing system comprising:
    one or more computer systems comprising one or more hardware processors and storage media; and
    instructions stored in the storage media and which, when executed by the computing system, cause the computing system to perform a method comprising:
        determining a set of fermentation parameters, comprising a set of ingredients and a set of microbial cultures;
        determining a metabolite composition based on the set of fermentation parameters, using a microbial model;
        determining a set of sensory attributes, comprising at least one of flavor or odor, based on the metabolite composition, using a sensory attribute model; and
        predicting a new set of fermentation parameters based on a comparison between the set of sensory attributes and a set of target attributes.

2. The computing system of claim 1, wherein the microbial model comprises a neural network trained on experimentally-derived metabolite compositions produced by each of a set of training fermentation parameters.

3. The computing system of claim 1, wherein the sensory attribute model comprises a neural network trained on observed sensory attributes associated with each of a set of training metabolite compositions.

4. The computing system of claim 3, wherein the set of sensory attributes comprise at least one of: aroma sensed at an olfactory bulb, retronasal aroma, or orthonasal aroma.

5. The computing system of claim 3, wherein the set of sensory attributes comprise a set of flavor classes, wherein a predicted value for each flavor class is indicative of a relative observed intensity of the respective flavor class.

6. The computing system of claim 1, wherein the new set of fermentation parameters is predicted using Bayesian optimization.

7. The computing system of claim 1, wherein the new set of fermentation parameters is predicted using a neural network.

8. The computing system of claim 1, wherein the new set of fermentation parameters is predicted using exploration-exploitation techniques.

9. The computing system of claim 1, wherein the new set of fermentation parameters is predicted by:
   determining a set of deviant sensory attributes based on the comparison;
   determining a subset of metabolites contributing to the set of deviant sensory attributes; and
   determining an adjustment to the set of fermentation parameters based on the subset of metabolites.

10. The computing system of claim 9, wherein the subset of metabolites is determined using interpretable deep learning.

11. The computing system of claim 9, wherein determining the adjustment comprises:
   determining a set of metabolic features associated with the subset of metabolites from the microbial model; and
   determining the adjustment based on the set of metabolite features.

\* \* \* \* \*